United States Patent [19]

Gemmill, Jr.

[11] 4,193,882

[45] Mar. 18, 1980

[54] CORROSION INHIBITED LUBRICANT COMPOSITION

[75] Inventor: Robert M. Gemmill, Jr., Pitman, N.J.

[73] Assignee: Mobil Oil Corporation, New York, N.Y.

[21] Appl. No.: 952,919

[22] Filed: Oct. 19, 1978

Related U.S. Application Data

[63] Continuation-in-part of Ser. No. 572,480, Apr. 28, 1975, abandoned, which is a continuation-in-part of Ser. No. 377,004, Jul. 6, 1973, abandoned.

[51] Int. Cl.$^2$ .............................................. C10M 1/38
[52] U.S. Cl. .................................. 252/47.5; 252/391; 548/142
[58] Field of Search .............................. 252/47.5, 391; 260/239.95, 302 SD

[56] References Cited

U.S. PATENT DOCUMENTS

| | | | |
|---|---|---|---|
| 2,836,564 | 5/1958 | Roberts et al. | 252/47.5 |
| 3,519,564 | 7/1970 | Vogel | 252/47.5 |
| 3,914,241 | 10/1975 | Elliott et al. | 252/32.7 E X |
| 3,929,652 | 12/1975 | Seni et al. | 252/47.5 X |
| 3,977,986 | 8/1976 | Conte, Sr. et al. | 252/47.5 X |
| 4,104,179 | 8/1978 | Colclough | 252/47.5 X |
| 4,136,043 | 1/1979 | Davis | 252/47.5 |
| 4,140,643 | 2/1979 | Davis | 252/47.5 |

*Primary Examiner*—Andrew Metz
*Attorney, Agent, or Firm*—Charles A. Huggett; Raymond W. Barclay; Thomas S. Szatkowski

[57] ABSTRACT

Lubricant compositions containing, in an amount sufficient to inhibit metal corrosion, the reaction product of oleic acid and 2,5-dimercapto-1,3,4-thiadiazole.

8 Claims, No Drawings

CORROSION INHIBITED LUBRICANT COMPOSITION

CROSS-REFERENCE TO RELATED APPLICATION

This application is a continuation-in-part of copending application Ser. No. 572,480, filed Apr. 28, 1975, now abandoned which in turn is a continuation-in-part of application Ser. No. 377,004, filed July 6, 1973, and now abandoned.

BACKGROUND OF THE INVENTION

1. Field of the Invention

This invention relates to lubricant compositions and, in one of its aspects, relates more particularly to lubricant compositions having improved properties for prevention of metal corrosion.

Still more particularly, in this aspect, the invention relates to lubricant compositions in the form of lubricating oils and greases containing additives effective for inhibiting metal corrosion.

2. Description of the Prior Art

The prior art has long recognized that lubricants, in the form of lubricating oils and greases, apart from performing their intended functions of lubricating metal parts, also exhibit the characteristic of permitting corrosion of metal surfaces with which they may come into contact. In order to control such corrosion, various additives have been suggested. Some of these additives have not proved to afford any appreciable improvement, while others, although more effective, have been found to be too costly.

One such prior art corrosion inhibitor is described in U.S. Pat. No. 2,836,564 as condensation products of alpha halogenated mono-carboxylic acid with 2,5-dimercapto-1,3,4-thiadiazole. Such materials are relatively insoluble in lubricating oils.

SUMMARY OF THE INVENTION

It has now been found that certain compounds which are probably isomeric with those of the cited patent exhibit markedly better solubility and higher values for corrosion inhibition. Data set out below in connection with the description of specific embodiments show these differences by strictly comparable data in that the alkyl chains derived from fatty acids are identical at 18 carbon atoms. It is particularly surprising that solubility varies in compounds having identity of alkyl groups which are generally regarded as providing solubility in oil.

In accordance with the present invention, lubricant compositions are provided containing, in an amount sufficient to inhibit metal corrosion, the reaction product of oleic acid and 2,5-dimercapto-1,3,4-thiadiazole. These reaction product additives, as more fully hereinafter described, are outstandingly effective in inhibiting the metal corrosion properties of lubricant and are also economical to use.

The aforementioned reaction products may be incorporated in any lubricating media which may comprise liquid hydrocarbon oils, in the form of either a mineral oil or a synthetic oil, or in the form of a grease in which any of the aforementioned oils are employed as a vehicle. In general, mineral oils, employed as the lubricant, or grease vehicle, may be of any suitable lubricating viscosity range, as, for example, from about 45 SSU at 100° F. to about 6000 SSU at 100° F., and, preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils or in combination therewith, various compounds of this type may be successfuly utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylether, etc.

The oleic acid and the 2,5-dimercapto-1,3,4-thiadiazole are reacted in a mol ratio of from 1:1 to about 2:1. In general, the reaction may be carried out at a temperature from about 150° C. to about 200° C., and preferably at a temperature from about 170° C. to about 200° C. The reaction product of the oleic acid and the 2,5-dimercapto-1,3,4-thiadiazole may be incorporated in the lubricant in any amount effective for inhibiting metal corrosion. In many instances, the reaction product may be incorporated in the lubricant in an amount from about 0.1 to about 1.0%, and preferably, in an amount from about 0.1 to about 0.5%, by weight, of the total lubricant composition.

The reaction between the oleic acid and the 2,5-dimercapto-1,3,4,-thiadiazole, in a 1:1 mol ratio, may be illustrated as follows:

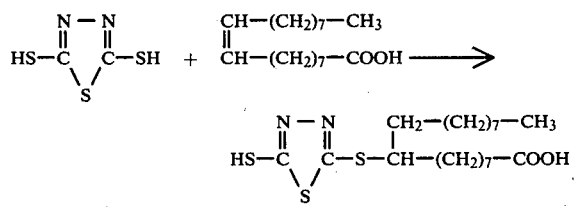

The reaction between the oleic acid and the 2,5-dimercapto-1,3,4-thiadiazole, in a 2:1 mol ratio may be illustrated as follows:

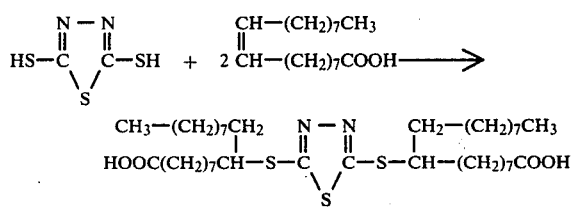

DESCRIPTION OF SPECIFIC EMBODIMENTS

The following examples and comparative data will serve to illustrate the novel metal corrosion inhibiting reaction products of the present invention, the method for their preparation and their utility in lubricating media, preferably as anti-rust agents and copper-passivators.

EXAMPLE 1

A mixture of 141 grams (0.51 mol) of oleic acid and 75 grams (0.5 mol) 2,5-dimercapto-1,3,4-thiadiazole was reacted at a temperature between about 170° C. and 185° C. for a period of about 26 hours to form a viscous, dark red-brown fluid product. Product empirical evaluation and performance data are shown in the following Tables.

EXAMPLE 2

A mixture of 141 grams (0.5 mol) of oleic acid and 37.5 grams (0.25 mol) of 2,5-dimercapto-1,3,4-thiadiazole was reacted at a temperature between about 195° C. and 205° C. for a period of about 17 hours to form a viscous, dark red-brown fluid product. Product empirical evaluation and performance data are shown in the following Tables.

Upon examination by infra-red absorption, the spectra of products from Examples 1 and 2 show reduction in oleic acid unsaturated bonds by sharply reduced absorption due to olefinic bonds. Absorption attributable to carboxylic acid groups indicates these groups are retained through the reaction. These IR spectra and the acid numbers are reported in Table I lead to conclusion that the product is an olefinmercaptan adduct rather than a thioester

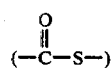

which could be postulated as a product of a reaction which evolves water. No water was evolved as by-product of the reaction in either example.

TABLE I

| | Product Analysis | | | |
|---|---|---|---|---|
| | Example I | | Example 2 | |
| | Found | Calc. | Found | Calc. |
| Mol. Wt. | 735. | 435 | 767. | 714. |
| Acid No. | 131. | 130. | 115. | 157. |
| %Carbon | 58.86 | 55.56 | 67.40 | 63.84 |
| % Hydrogen | 8.81 | 8.33 | 10.30 | 9.80 |
| % Oxygen | 8.04 | 7.41 | 7.20 | 9.00 |
| % Nitrogen | 6.50 | 6.48 | 3.20 | 3.92 |
| % Sulfur | 17.40 | 22.22 | 10.00 | 13.44 |

TABLE II

Product Performance
ASLE Wet Corrosion Test and ASTM D130-6 Copper Corrosion Test

| Blend Components Wt. % | 1 | 2 | 3 |
|---|---|---|---|
| *Lubricating Oil Stock | 96.5 | 96.4 | 96.4 |
| Sulfurized Isobutylene E.P. Additive | 3.5 | 3.5 | 3.5 |
| Example 1 | | 0.1 | |
| Example 2 | | | 0.1 |
| Rating | | | |
| Copper- vapor | 2C | 2C | 2A |
| Copper- liquid | 4A | 3B | 3B |
| Sludge | Lt. | Tr. | Nil |
| ASTM D130-6 Copper Corrosion | 3A | 2A | 2A |

*Solvent-refined Mid-continent S.A.E. 90 oil

The efficacy of the reaction products of the oleic acid and 2,5-dimercapto-1,3,4-thiadiazole will be apparent from the above performance data with respect to reduced copper corrosion in vapor and liquid states and also sludge formation.

TABLE III

Antirust Evaluation
ASTM D665 Series Rust Tests

| Blend Components Wt. % | Test A | Test B | Test C |
|---|---|---|---|
| *Lubricating Oil Stock | 100. | 99.5 | 99.5 |
| Example 1 | | 0.5 | |
| Example 2 | | | 0.5 |
| D665-2 Test (Duplicate Runs) | | | |
| 48 hours, 140° F. | Med. | Pass | Pass |
| dist. H$_2$O | Med. | Pass | Pass |
| D665-4 Test (Duplicate Runs) | | | |
| 48 hours, 140° F. | 90% | 30% | Pass |
| salt H$_2$O | 80% | 40% | Pass |

Rating Code: Pass - no rust
Light - no more than 6 spots
Medium - up to 5% of surface spotted
Severe - more than 5% of surface spotted
*Solvent-refined Mid-Continent S.A.E. 30 oil The above comparative data illustrates the efficacy of the oleic acid-2,5-dimercapto-1,3,4- thiadiazole reaction product in inhibiting rust formation.

Humidity Chamber Rust Tests

This is a general purpose and severe rust test. It utilizes a humidity chamber operated at 120° F. and 97–98% Relative Humidity with an air circulation rate of 150 cubic feet per minute. The test panels are 2"×4"×1/8" polished steel plates of SAE 1010 steel of a 10 micron finish.

The test is performed by first cleaning a new panel in naptha, absolute methanol and xylene in that order. The air dried panel is then dipped in a test formulation for one minute and then "drip-dried" for two hours prior to insertion into the chamber. The panels are suspended in a vertical position within the chamber and can be continuously monitored through the glass dome of the chamber.

The severity of the test can be judged by the rapid rusting rate (1 hour) of a panel coated only with a solvent-refined Mid-Continent S.A.E. 30 oil base stock compared to complete rust inhibition for periods up to 5 days when utilizing a rust inhibitor in concentrations of 0.5 to 4.0%.

The following data indicate the formulations tested and the ratings show the number of days to achieve the first indication of rust and the degree of rust at that time. The degree of rust is given since some antirust agents will allow only a gradual rusting rate while some allow a sudden, catastrophic rusting rate after their inhibiting ability is depleted.

TABLE IV

| Formulation | Days to First Rust-Rating at that time |
|---|---|
| 1. Lubricating Oil Stock | 0 - Heavy (heavy rust |

TABLE IV-continued

| Formulation | | Days to First Rust-Rating at that time |
|---|---|---|
| | | in one hour) |
| 2. Lubricating Oil Stock | +0.5% Ex.1 | 3 - Trace |
| 3. Lubricating Oil Stock | +0.5% Ex. 2 | 5 - Light |

The humidity chamber rust rating code is as follows:
Trace—1 or 2 spots on surface
Light—less than 6 spots on surface
Moderate—6 spots to light distribution
heavy—more than light distribution to castastrophic rust.

The comparative data of the humidity chamber tests illustrate the efficacy of the novel reaction products of the present invention in inhibiting metal corrosion.

The prior art discussed above has suggested the use of isomers of the novel reaction product of the present invention, as corrosion inhibitors in lubricating media. In this respect, comparative data were obtained with regard to the corrosion-inhibiting properties of an isomer, such as disclosed in U.S. Pat. No. 2,836,564, which are condensation products of an alpha halogenated aliphatic stearic acid with 2,5-dimercapto-1,3,4-thiadiazole.

The aforementioned condensation product of U.S. Pat. No. 2,836,564 was prepared in accordance with Example 1 of the patent and was carried out in the exact manner disclosed in the patent. More specifically, 15 grams (0.1 mol) of 2,5-dimercapto-1,3,4-thiadiazole in 100 cc. ethanol was treated with 12.8 grams (0.2 mole) of KOH (87.9%) dissolved in 90 cc. ethanol. To the cooled suspension-solution were added 72.7 grams (0.2 mole) of alpha-brom-stearic acid and 11.2 grams KOH dissolved in 110 cc. ethanol with an additional 90 cc. ethanol. The mixture was stirred and warmed on a steam bath and refluxed for 4 hours. The mixture was then diluted with about an equal volume of water and treated with an excess of concentrated HCl. The product, set free as an oil, was extracted with hexane and the hexane extract washed once with water and then with 20% ethanol. The hexane solution was then dried over sodium sulfate, filtered and freed of hexane by evaporation. Recrystallization from a benzene-hexane solution yielded a light buff colored solid havng a melting point of 81° C.

The alpha-brom-stearic acid employed in Example 1 of the aforementioned patent was prepared from stearic acid, thionyl chloride and bromine.

A comparison of rust-inhibiting properties was made between the product obtained in accordance with Example 1 of U.S. Pat No. 2,836,564 and that obtained in accordance with Example 2 (supra) of the present invention by the procedure of ASTM D665-4 Rust Test. The test was run at 140° F., for 48 hours using salt $H_2O$. The results obtained are set forth in the following Table V.

TABLE V

| Rust Inhibitor | Solubility in Solvent-Refined Mid-Continent SAE 30 Oil | ASTM D665-4 Rust Test 48 hours, 140° F. salt $H_2O$ |
|---|---|---|
| Example 1 of U.S. Pat. No. 2,836,564 | 0.1% Trace precipitate | Severe - 15% rust / Severe - 15% rust |
| Example 1 of U.S. Pat. No. 2,836,564 | 0.5% Heavy to total precipitate - insoluble | Could not evaluate in this base oil |
| Example 2 (supra) | 0.5% Trace precipitate-Hazy | Light - 3 spots / Moderate - 5% rust |

Omitted from Table V is an attempted evaluation of the product of Example 2 of this invention at 0.1% concentration in the oil specified in Table V. Failure of analytical equipment aborted that evaluation. Repeat was seen to be unjustified because low solubility of the product of U.S. Pat. No. 2,836,564 in this base stock makes the comparison data ambiguous. The data of Table V are strongly indicative of better rust prevention by compositions according to this invention in that the maximum amount of the prior art additive soluble in the oil provided little rust inhibition. The product of this invention could be dissolved to an extent which provided effective prevention.

Search for a base stock in which the products could be meaningfully compared included attempts to dissolve the product of U.S. Pat. No. 2,836,564 in naphthenic, aromatic and ester oils; without success. A comparison was achieved in solvent refined Mid-Continent SAE 30 oil containing 1% of a succinimide dispersant. The product of the said patent was insoluble in the base oil without dispersant. The product of this invention formed hazy solutions but did not precipitate in the absence of dispersant.

The dispersant comprised a bis-succinimide reaction product of 2 moles of polybutenyl succinic anhydride and 1 mole of tetraethylenepentamine, in which the polybutenyl group has a molecule weight of 900. A comparison of corrosion-inhibiting properties was made, as previously stated, between the product of Example 2 of the present invention and that of the product of Example 1 of U.S. Pat. No. 2,836,564, employing the aforementioned standard ASTM D665-4 rust test run for 48 hours at 140° F. using the salt $H_2O$. The comparative results obtained are set forth in the following table, and serve to indicate the superiority in corrosion-inhibiting properties of the reaction products of the present invention over those of the most pertinent prior art.

TABLE VI

| Comparison of Rust Inhibition in SAE 30 Mid-Continent Plus 1% Succinimide Dispersant | | |
|---|---|---|
| | ASTM D665-4 Rust Test 48 hours, 140° F. salt $H_2O$ | |
| Rust Inhibitor Conc., Wt. % | Product of Example 2 | Product of Example 1 of U.S. Pat. No. 2,836,564 |
| Zero | | Moderate - 5% Rust |
| 0.10 | Pass | Light - 2% Rust |
| 0.17 | Pass | Light - 1% Rust |

TABLE VI-continued

Comparison of Rust Inhibition in SAE 30 Mid-Continent Plus 1% Succinimide Dispersant

| | ASTM D665-4 Rust Test 48 hours, 140° F. salt H$_2$O | |
|---|---|---|
| Rust Inhibitor Conc., Wt. % | Product of Example 2 | Product of Example 1 of U.S. Pat. No. 2,836,564 |
| 0.50 | Pass | Pass |

While this invention has been described with reference to preferred compositions and components therefor, it will be understood, by those skilled in the art, that departure from the preferred embodiments can be effectively made and are within the scope of the specification.

I claim:

1. A lubricant composition comprising: a major proportion of a lubricating medium selected from the group consisting of oils of lubricating viscosity and greases thereof; and, in an amount sufficient to inhibit metal corrosion, a compound having the formula:

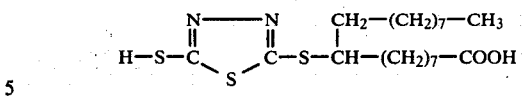

2. A composition as defined in claim 1 wherein said lubricating medium comprises a mineral oil-based composition.

3. A composition as defined in claim 1, wherein said lubricating medium comprises a synthetic oil-based composition.

4. A composition as defined in claim 1 wherein said lubricating medium comprises an oil of lubricating viscosity in the range from about 45 SSU at 100° F. to about 6000 SSU at 100° F.

5. A composition as defined in claim 1 wherein said lubricating medium comprises an oil of lubricating viscosity in the range from about 50 SSU at 210° F. to about 250 SSU at 210° F.

6. A composition as defined in claim 1 wherein said metal corrosion-inhibiting compound is present in an amount from about 0.1 to about 1.0%, by weight.

7. A composition as defined in claim 1 wherein said metal corrosion-inhibiting compound is present in an amount from 0.1% to about 0.5%, by weight.

8. A process which comprises reacting oleic acid and 2,5-dimercapto-1,3,4-thiadiazole at a temperature from about 150° C. to about 200° C. and in a mole ratio of 1:1.

* * * * *